US010189118B2

(12) United States Patent
Cai et al.

(10) Patent No.: US 10,189,118 B2
(45) Date of Patent: Jan. 29, 2019

(54) METHOD AND APPARATUS FOR EVALUATING AN ULTRASONIC WELD JUNCTION

(71) Applicant: GM GLOBAL TECHNOLOGY OPERATIONS LLC, Detroit, MI (US)

(72) Inventors: Wayne W. Cai, Troy, MI (US); Debejyo Chakraborty, Novi, MI (US); Qian Lin, Troy, MI (US); John M. Moote, Plymouth, MI (US); Anthony Ottomano, Warren, MI (US); Teresa J. Rinker, Royal Oak, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 299 days.

(21) Appl. No.: 15/174,288

(22) Filed: Jun. 6, 2016

(65) Prior Publication Data

US 2017/0348804 A1    Dec. 7, 2017

(51) Int. Cl.
| | |
|---|---|
| *B23K 1/06* | (2006.01) |
| *B23K 31/12* | (2006.01) |
| *G01N 25/72* | (2006.01) |
| *G01N 27/416* | (2006.01) |
| *G01R 31/36* | (2006.01) |
| *B23K 20/10* | (2006.01) |

(52) U.S. Cl.
CPC ........... *B23K 31/125* (2013.01); *G01N 25/72* (2013.01); *G01N 27/416* (2013.01); *G01R 31/36* (2013.01); *B23K 20/10* (2013.01)

(58) Field of Classification Search
CPC .............. B23K 31/125; B23K 1/06; B23K 20/10–20/106; B23K 20/12–20/1215; B23K 20/1285–20/1295; G01R 31/36; G01N 25/72; G01N 27/416
USPC ...... 228/8–12, 102–105, 58, 901, 110.1, 1.1, 228/2.1–2.3, 112.1–114.5
See application file for complete search history.

(56) References Cited

U.S. PATENT DOCUMENTS 3,459,918 A * 8/1969 Rzant ..................... H01R 43/02
219/56.21
5,042,460 A * 8/1991 Sakurai ............ A61B 17/22012
310/316.01

(Continued)

FOREIGN PATENT DOCUMENTS

JP          06031461 A  *  2/1994
JP          10064508 A  *  3/1998

(Continued)

*Primary Examiner* — Kiley S Stoner
(74) *Attorney, Agent, or Firm* — Quinn IP Law

(57) ABSTRACT

A method and a test fixture for evaluating a battery cell are described, wherein the battery cell is composed of a cell body having a plurality of electrode foils that are joined to both a positive terminal and a negative terminal at weld junctions. The method includes retaining the cell body of the battery cell in a first clamping device and gripping one of the positive and negative terminals in a terminal gripper. A dynamic stress end effector coupled to the terminal gripper is employed to apply a vibrational excitation load to the one of the positive and negative terminals. Impedance between the positive terminal and the negative terminal is monitored via a controller, and integrity of the weld junction of the one of the positive and negative terminals is evaluated based upon the impedance.

15 Claims, 4 Drawing Sheets

(56) References Cited

U.S. PATENT DOCUMENTS

| | | | | |
|---|---|---|---|---|
| 5,963,022 A * | 10/1999 | Buda | | B23K 11/258 |
| | | | | 219/110 |
| 9,882,192 B2 * | 1/2018 | Khakhalev | | B23K 20/10 |
| 2004/0061503 A1 * | 4/2004 | Morimoto | | B60K 6/28 |
| | | | | 324/418 |
| 2008/0265004 A1 * | 10/2008 | Stroh | | B23K 20/10 |
| | | | | 228/110.1 |
| 2010/0140228 A1 * | 6/2010 | Suzuki | | B23K 11/0026 |
| | | | | 219/117.1 |
| 2011/0187329 A1 * | 8/2011 | Majinna | | H01M 10/48 |
| | | | | 320/149 |
| 2013/0105556 A1 * | 5/2013 | Abell | | G05B 23/0221 |
| | | | | 228/1.1 |
| 2013/0105557 A1 * | 5/2013 | Spicer | | B23K 20/10 |
| | | | | 228/104 |
| 2013/0187671 A1 * | 7/2013 | Widhalm | | G01R 31/36 |
| | | | | 324/691 |
| 2013/0306216 A1 * | 11/2013 | Cai | | B23K 20/10 |
| | | | | 156/64 |
| 2014/0015535 A1 * | 1/2014 | Lopez | | G01R 31/362 |
| | | | | 324/433 |
| 2014/0138012 A1 * | 5/2014 | Spicer | | B06B 3/00 |
| | | | | 156/64 |
| 2015/0069829 A1 * | 3/2015 | Dulle | | B60R 16/03 |
| | | | | 307/9.1 |
| 2015/0147598 A1 * | 5/2015 | Inoue | | H01M 2/26 |
| | | | | 429/7 |
| 2015/0165673 A1 * | 6/2015 | Spicer | | B23K 20/10 |
| | | | | 156/64 |
| 2015/0168942 A1 * | 6/2015 | Spicer | | G05B 19/4065 |
| | | | | 700/160 |
| 2015/0375334 A1 * | 12/2015 | Balogh | | B23K 20/106 |
| | | | | 228/102 |
| 2015/0379894 A1 * | 12/2015 | Becker | | G09B 9/00 |
| | | | | 219/124.1 |
| 2016/0039053 A1 * | 2/2016 | Becker | | G09B 19/24 |
| | | | | 228/102 |
| 2016/0077159 A1 * | 3/2016 | Petrucelli | | G01R 31/362 |
| | | | | 324/426 |
| 2016/0126532 A1 * | 5/2016 | Eaglesham | | H01M 4/58 |
| | | | | 429/7 |
| 2017/0184522 A1 * | 6/2017 | Kise | | H01M 10/4285 |
| 2017/0202604 A1 * | 7/2017 | Tanigami | | A61B 17/32006 |
| 2017/0315100 A1 * | 11/2017 | Cai | | G01N 3/08 |
| 2017/0322168 A1 * | 11/2017 | Lupienski | | G01N 27/20 |
| 2018/0196105 A1 * | 7/2018 | Inukai | | G01R 31/36 |
| 2018/0233772 A1 * | 8/2018 | Sasaki | | G01R 31/36 |

FOREIGN PATENT DOCUMENTS

| | | | | |
|---|---|---|---|---|
| JP | | 2003307480 A | * 10/2003 | |
| WO | WO-2015059879 A1 | * 4/2015 | | H01M 10/48 |

* cited by examiner

METHOD AND APPARATUS FOR EVALUATING AN ULTRASONIC WELD JUNCTION

TECHNICAL FIELD

The present disclosure relates to cells of a battery pack, and weld junctions thereof.

BACKGROUND

A battery pack typically includes multiple rechargeable battery cells that are connected in series or parallel to store and supply electric power to a distribution system. Each battery cell includes a plurality of electrode foils having alternately-placed positive and negative charge portions. The electrode foils are separated by separator material and enclosed within a sealed outer pouch that is filled with an electrolyte solution. The separator material, e.g., polyethylene and/or polypropylene film, helps prevent an electrical short condition while permitting the free transfer of electrical charge between electrode foils.

Positive and negative terminals each extend a short distance outside of the sealed pouch for each battery cell. The positive charge portions of the electrode foils are ultrasonically welded together and welded to the positive terminal, and the negative charge portions of the electrode foils are ultrasonically welded together and welded to the negative terminal. The ultrasonic welds are internal to and contained within the sealed outer pouch. Process capability of the ultrasonic welding process that forms the internal weld may be subject to variation due to ultrasonic welder variations and other factors.

SUMMARY

A method and a test fixture for evaluating a battery cell are described, wherein the battery cell is composed of a cell body having a plurality of electrode foils that are joined to both a positive terminal and a negative terminal at weld junctions. The method includes retaining the cell body of the battery cell in a first clamping device and gripping one of the positive and negative terminals in a terminal gripper. A dynamic stress end effector coupled to the terminal gripper is employed to apply a vibrational excitation load to the one of the positive and negative terminals. Impedance between the positive terminal and the negative terminal is monitored via a controller, and integrity of the weld junction of the one of the positive and negative terminals is evaluated based upon the impedance.

The above features and advantages, and other features and advantages, of the present teachings are readily apparent from the following detailed description of some of the best modes and other embodiments for carrying out the present teachings, as defined in the appended claims, when taken in connection with the accompanying drawings.

BRIEF DESCRIPTION OF THE DRAWINGS

One or more embodiments will now be described, by way of example, with reference to the accompanying drawings, in which.

DETAILED DESCRIPTION

Figure 1:
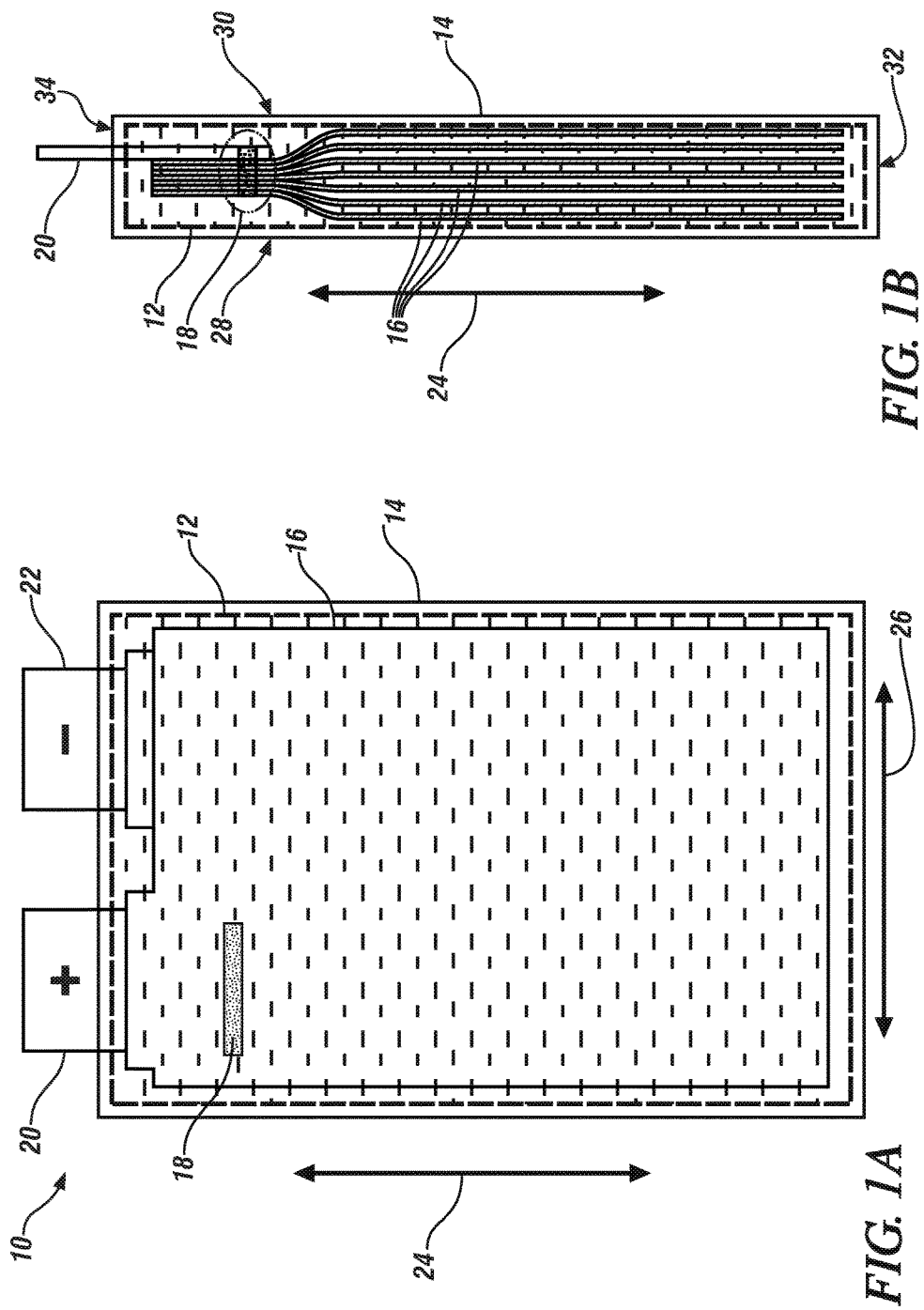
FIGS. 1A and 1B schematically illustrate a front view and a corresponding side view of selected elements of a single battery cell, in accordance with the disclosure.

Referring now to the drawings, which are provided for the purpose of illustrating certain exemplary embodiments only and not for the purpose of limiting the same, FIGS. 1A and 1B schematically illustrate a front view and a corresponding side view, respectively, of selected elements of a single battery cell 10. Like numerals indicate like or corresponding parts throughout the several views. Those having ordinary skill in the art will recognize that terms such as "horizontal", "vertical", "above," "below,", "top," "bottom," etc., are used descriptively for the figures, and do not represent limitations on the scope of the disclosure, as defined by the appended claims. The term "end effector" is defined as a device that may be controlled to accomplish a pre-defined task in response to a control command, and may be mechanically actuated, electro-mechanically actuated, pneumatically actuated, or may employ another actuation system.

The battery cell 10 includes a cell body 14 that includes a plurality of electrode foils 16 in plate form that are arranged in a vertical stack and contained within a sealed pouch 12 that is filled with electrolytic fluid in one embodiment. Negative charge portions of the plurality of electrode foils 16 are ultrasonically welded together and welded to a negative terminal 22, preferably employing ultrasonic welding methods. Similarly, positive charge portions of the electrode foils 16 are ultrasonically welded together and welded to the positive terminal 20. A weld junction 18 is shown, and is a first of two weld junctions. The weld junction 18 mechanically and electrically joins the electrode foils 16 and the positive terminal 20, and is preferably formed parallel to a lateral axis 26, although the concepts described herein are not so limited. The weld junction 18 between the electrode foils 16 and the positive terminal 20 may be in the form of a lap weld junction, although the concepts described herein are not so limited. A second of two weld junctions (not shown) joins the negative charge portions of the electrode foils 16 and the negative terminal 22. The battery cell 10 may be nominally described in terms of a first face portion 28, a second face portion 30, a bottom portion 32 and a top portion 34. The lateral axis 26 extends in a horizontal direction, as shown, between the first face portion 28 and the second face portion 30. A longitudinal axis 24 extends between the bottom portion 32 and the top portion 34 in a vertical direction as shown and orthogonal to the lateral axis 26. Other details related to the battery cell 10 are known to one of ordinary skill in the art. In one embodiment, the single battery cell 10 is a lithium-ion battery cell that is rechargeable, although the concepts described herein may be applied to other battery cell configurations that are fabricated in a manner described herein. Alternatively, the battery cell 10 may be configured as a cylindrical device having terminals extending from one of its ends. Alternatively, the battery cell 10 may be configured as a brick-shaped device having terminals extending from one of its ends. The concepts described herein apply to any configuration of the battery cell 10.

Figure 2:
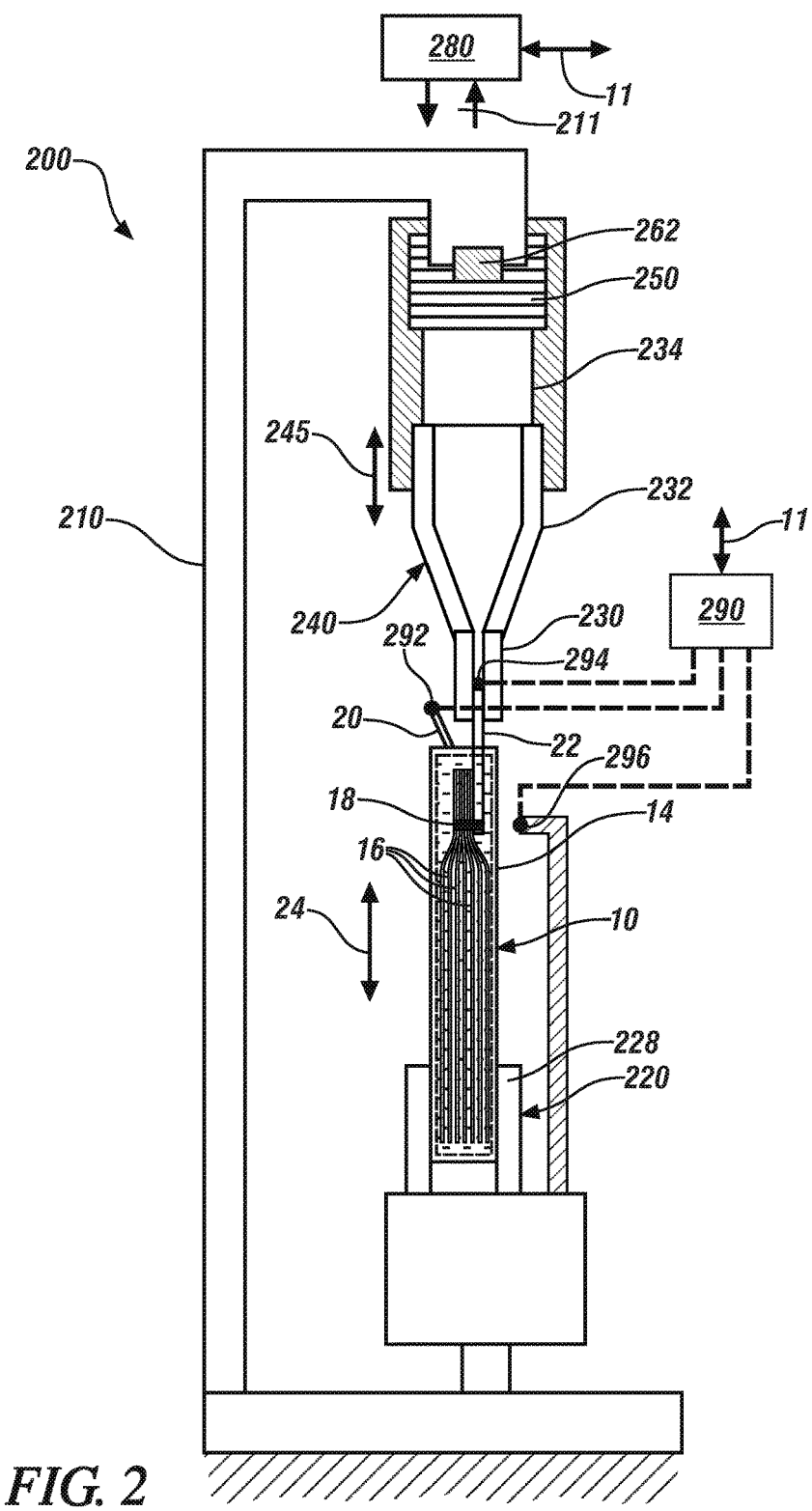
FIG. 2 schematically shows a first embodiment of a test fixture for evaluating a workpiece, including a first clamping device, a dynamic stress end effector, a test fixture controller and a cell monitoring controller configured to monitor impedance across terminals of a battery cell, in accordance with the disclosure.

FIG. 2 schematically shows a first embodiment of a test fixture 200 for evaluating a workpiece, wherein the workpiece is an embodiment of the battery cell 10 described with reference to FIGS. 1A and 1B. As shown, the battery cell 10 includes the positive terminal 20, the negative terminal 22, cell body 14 including a plurality of electric foils 16, and the weld junction 18 that joins the electrode foils 16 of the cell body 14 and the positive terminal 20. The second weld junction that joins the electrode foils 16 of the cell body 14 and the negative terminal 22 is not shown. The test fixture 200 includes a frame 210 on which is mounted a first clamping device 220, a dynamic stress end effector 240, a test fixture controller 280, and a cell monitoring controller 290. In one embodiment, the test fixture 200 further includes a thermal probe 296 that is configured to monitor temperature at or near the weld junction 18 of the battery cell 10. The test fixture 200 is disposed to apply a vibrational excitation load to each of the positive and negative terminals 20, 22 of the battery cell 10, and monitor parameters of the battery cell 10, as described herein.

The first clamping device 220 includes a gripping device 228 that is configured to retain a workpiece, which includes the cell body 14 of the battery cell 10 in one embodiment. The first clamping device 220 and gripping device 228 may be configured as a force-closure clamping device that exerts a normal force on the cell body 14 to effect its retention in one embodiment. Alternatively, the first clamping device 220 may be configured as a form-closure clamping device that accommodates geometric features of the cell body 14 of the battery cell 10 to effect its retention. Alternatively, the first clamping device 220 may be a combination of the force-closure clamping device and the form-closure clamping device. As shown, the first clamping device 220 and gripping device 228 are configured as a force-closure device, which may include a first plate section arranged in parallel with an opposed second plate section in one embodiment, wherein the first and second plate sections may be urged together to apply a gripping force on the cell body 14 of the battery cell 10. The relevant dimensions of the first clamping device 220 are preferably selected to accommodate dimensions of a specific embodiment of the cell body 14 of the battery cell 10. The gripping device 228 is disposed to impose a clamping force on the cell body 14 when the battery cell 10 is inserted into the clamping device 220. The gripping device 228 may employ any suitable force or pressure generated device, such as a pneumatically-powered cylinder having two-way control capability to apply and remove the clamping force. The applied clamping force mechanically retains the inserted battery cell 10 for purposes of performing dynamic and static testing on the battery cell 10, as described herein. The removal of the clamping force urges the first plate section away from the second plate section to permit removal of the inserted battery cell 10. Details related to clamping mechanisms for test fixtures are known to one of ordinary skill in the art, and thus not described in detail.

The dynamic stress end effector 240 includes a terminal gripper 230 that is mechanically coupled to a dynamic stress mechanism 250 via a waveguide device 232 and a force coupler 234. The terminal gripper 230 is preferably located adjacently above the first clamping device 220 (as shown), thus permitting it to interact with and mechanically grip one of the positive and negative terminals 20, 22 of the battery cell 10 when inserted into the first clamping device 220. The dynamic stress mechanism 250 is a repetitive stress-applying device that generates a vibrational excitation load that is transferred through the waveguide 232, the force coupler 234, and the terminal gripper 230 to the one of the positive and negative terminals 20, 22 of the battery cell 10 that has been gripped. The dynamic stress mechanism 250 is preferably a piezo-electric device that is capable of generating high frequency vibration that is propagated through the force coupler 234 and the waveguide 232 to the terminal gripper 230. A load cell 262 may be disposed to monitor the vibrational excitation load. Load cells and associated linear measurement systems are known to one of ordinary skill in the art, and thus not described in detail herein. The vibrational excitation load is preferably applied in a direction that is parallel to the longitudinal axis 24 of the battery cell 10 as indicated by arrow 245. The vibrational excitation load may be in the in the form of an ultrasonic vibrational load. Alternatively, the vibrational excitation load may be applied horizontally, i.e., in a direction that is orthogonal to the longitudinal axis 24 of the battery cell 10. In one embodiment, the ultrasonic vibrational load includes an oscillatory motion that is applied at a frequency that is within a range between 10 kHz and 100 kHz, at an amplitude that is preferably within a range between several micrometers and one hundred micrometers, for a duration of time between 0.5 s and 10 s. Other suitable vibrational excitation loads that are described in terms of vibrational frequencies, amplitudes and durations may be selected, depending upon the particular design of the embodiment of the battery cell 10, with a process for such selection known to one of ordinary skill in the art.

The cell monitoring controller 290 is disposed to electrically connect to the positive and negative terminals 20, 22 of the battery cell 10 via probes 292, 294, respectively. Probes 292, 294 are preferably fabricated from materials that are similar to the materials of the positive and negative terminals 20, 22 so as to not introduce signal distortion due to mechanical coupling of dissimilar metals. As such, when terminal 20 is fabricated from copper, the associated probe 292 is fabricated from copper or a copper alloy. Likewise, when terminal 22 is fabricated from aluminum, the associated probe 294 is fabricated from aluminum or an aluminum alloy. Furthermore, probe 294 is preferably integrated into the terminal gripper 230 of the dynamic stress end effector 240, with signal continuity to the cell monitoring controller 290 and electrical isolation from other elements.

The cell monitoring controller 290 includes an instruction set and associated circuitry to monitor impedance of the battery cell 10 as measured across the positive and negative terminals 20, 22. In one embodiment, the instruction set includes a form of electrochemical impedance spectroscopy (EIS), which may include applying an excitation signal in the form of a small amplitude AC current to the battery cell 10 via the positive and negative terminals 20, 22 and measuring current flow therethrough. Impedance across the battery cell 10 may be determined based upon the current flow. In one embodiment, the impedance across the battery cell 10 is monitored coincident with operation of the dynamic stress end effector 240 to apply a vibrational excitation load in one of the positive and negative terminals 20, 22 of the battery cell 10. Monitoring impedance of the battery cell 10 employing EIS or other similar methods is known to one of ordinary skill in the art.

In one embodiment, thermal probe 296 is configured to monitor temperature at or near the weld junction 18 of the battery cell 10. The thermal probe 296 may be disposed to monitor heat generation at or near the weld junction 18 of the battery cell 10, preferably during the operation of the dynamic stress end effector 240 to apply the vibrational excitation load in one of the positive and negative terminals 20, 22 of the battery cell 10. The thermal probe 296 may be a thermocouple, thermistor or another contact-based temperature sensor, an infrared camera, a laser temperature sensor, or another non-contact-based temperature sensor, or another suitable device capable of monitoring temperature.

The test fixture controller 280 communicates with the first clamping device 220, the dynamic stress end effector 240 and the cell monitoring controller 290 to monitor various sensors and generate control commands for various actuators to accomplish predetermined tasks.

The terms controller, control module, module, control, control unit, processor and similar terms refer to any one or various combinations of Application Specific Integrated Circuit(s) (ASIC), electronic circuit(s), central processing unit(s), e.g., microprocessor(s) and associated non-transitory memory component in the form of memory and storage devices (read only, programmable read only, random access, hard drive, etc.). The non-transitory memory component is capable of storing machine readable instructions in the form of one or more software or firmware programs or routines, combinational logic circuit(s), input/output circuit(s) and devices, signal conditioning and buffer circuitry and other components that can be accessed by one or more processors to provide a described functionality. Input/output circuit(s) and devices include analog/digital converters and related devices that monitor inputs from sensors, with such inputs monitored at a preset sampling frequency or in response to a triggering event. Software, firmware, programs, instructions, control routines, code, algorithms and similar terms mean any controller-executable instruction sets including calibrations and look-up tables. Each controller executes control routine(s) to provide desired functions, including monitoring inputs from sensing devices and other networked controllers and executing control and diagnostic instructions to control operation of actuators. Routines may be executed at regular intervals, or in response to occurrence of a triggering event. Communication between controllers, and communication between controllers, actuators and/or sensors may be accomplished using a direct wired point-to-point link, a networked communication bus link, a wireless link or any other suitable communication link, and is indicated by line 11. Communication includes exchanging data signals in any suitable form, including, for example, electrical signals via a conductive medium, electromagnetic signals via air, optical signals via optical waveguides, and the like. The data signals may include discrete, analog or digitized analog signals representing inputs from sensors, actuator commands, and communication between controllers. The term "signal" refers to any physically discernible indicator that conveys information, and may be any suitable waveform (e.g., electrical, optical, magnetic, mechanical or electromagnetic), such as DC, AC, sinusoidal-wave, triangular-wave, square-wave, vibration, and the like, that is capable of traveling through a medium.

Figure 3:
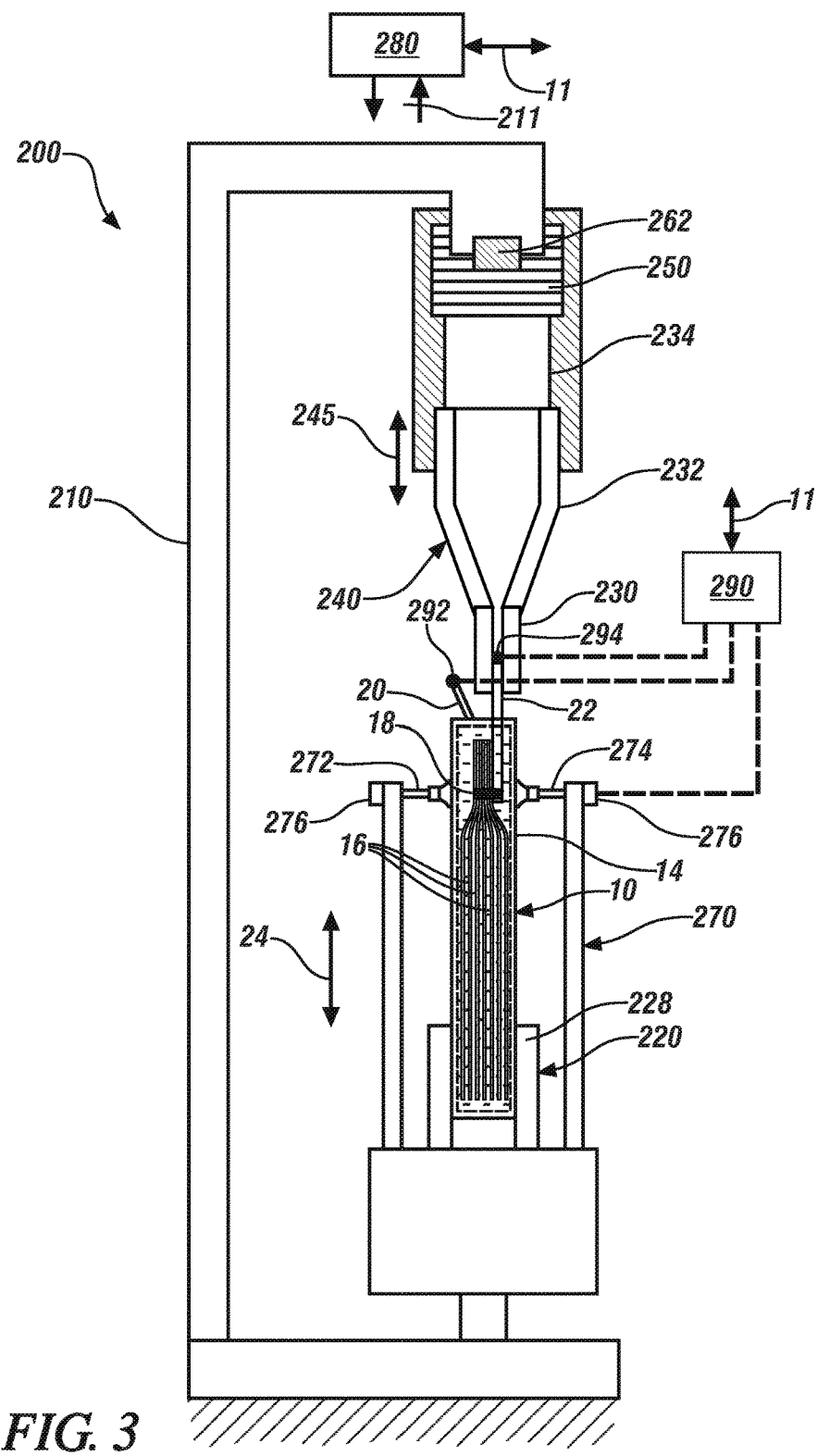
FIG. 3 schematically shows a second embodiment of a test fixture for evaluating a workpiece, including a first clamping device, a dynamic stress end effector, a test fixture controller, a cell monitoring controller configured to monitor impedance across terminals of a battery cell and a cell tensioning device, in accordance with the disclosure.

FIG. 3 schematically shows a second embodiment of a test fixture 300 for evaluating a workpiece, wherein the workpiece is an embodiment of the battery cell 10 described with reference to FIGS. 1A and 1B. The test fixture 300 is analogous to the test fixture 200 shown with reference to FIG. 2 in several respects. The test fixture 300 includes the first clamping device 220, the dynamic stress end effector 240, the test fixture controller 280, and a cell monitoring controller 295. The test fixture 300 further includes a cell tensioning device 270.

The cell tensioning device 270 preferably includes a first member 272, a second member 274 and one or multiple actuators 276. The first and second members 272, 274 each include a pneumatically-activated suction device or similar device that is capable of applying suction to a surface when activated by the actuators 276. The cell tensioning device 270 is disposed on the test fixture 300 such that the first member 272 and the second member 274 are positioned in opposed locations and adjacent to surfaces of the battery cell 10 at or near the respective weld junction, e.g., weld junction 18, when the battery cell 10 has been placed in the test fixture 300. When the actuators 276 are activated, e.g., by a signal from the cell monitoring controller 295, the first and second members 272, 274 are suitably positioned to exert a tensile force on the elements of the battery cell 10 at or near the weld junction 18. Such tensile force exerts a separating force on the electrode foils 16 of the cell body 14 and the respective terminal, e.g., the respective weld junction 18 that is associated with the positive terminal 20. The magnitude of the separating force is set to be less than the elastic limit or yield point for the weld junction. The separating force may cause an increase in the impedance across the positive and negative terminals 20, 22, which may be monitored and detected by the cell monitoring controller 295.

The cell monitoring controller 295 is analogous to the cell monitoring controller 290 described herein, and is disposed to electrically connect to the positive and negative terminals 20, 22 of the battery cell 10 via probes 292, 294, respectively and control the actuators 276 of the cell tensioning device 270. The cell monitoring controller 290 includes an instruction set and associated circuitry to monitor impedance of the battery cell 10 as measured across the positive and negative terminals 20, 22. In one embodiment, the instruction set includes a form of electrochemical impedance spectroscopy (EIS), which may include applying an excitation signal in the form of a small amplitude AC current to the battery cell 10 via the positive and negative terminals 20, 22 and measuring current flow therethrough. Impedance across the battery cell 10 may be determined based upon the current flow. In one embodiment, the impedance across the battery cell 10 is monitored coincident with operation of the cell tensioning device 270 to apply a tension load in one of the weld junctions, e.g., weld junction 18 of the battery cell 10.

Monitoring impedance of the battery cell 10 employing EIS or other similar methods preferably includes applying a current of known magnitude and monitoring voltage, and determining a magnitude for impedance based upon the relationship between current, voltage, and impedance, i.e., $V=I*R$. Applying a current and monitoring voltage is a preferred process for a battery cell because a battery cell is capable of accepting or delivering amounts of current that will provide small but measurable voltage changes. As appreciated, the intrinsic impedance of an embodiment of the battery cell 10 may be in the order of magnitude of 1 milli-ohm, and thus a change in impedance may be in the order of magnitude of micro-ohms due to the weld. In one embodiment, the applied current may be in the form of a sine wave current, and the output signal may thus be a sine wave voltage that is shifted in phase. The amplitude and amount of phase shift of the output signal in combination with the applied current may be evaluated to determine the magnitude of the battery cell impedance.

In one embodiment, a single-frequency sine wave current may be applied across the terminals of the battery cell 10, e.g., around 500 Hz in one embodiment, which yields a sine wave voltage having the same frequency but shifted in phase and amplitude. A non-integral (non-harmonic) vibratory signal may be introduced, e.g., 953 Hz in one embodiment. If the vibratory signal applies a change in the voltage-current relationship of the applied electrical signal, then there may be a fault in the weld. By moving the measured signal from the time to the frequency domain, the introduced signal (e.g., 953 Hz) is moved away from the applied frequency (e.g., 500 Hz), which can be analyzed on a frequency plot. Such operation provides a frequency discrimination of the impedance change that is caused by the applied frequency, and thus may be evaluated to determine the impedance change. This evaluation may be employed to determine the impedance, including any impedance change that may be attributable to weld quality. Additional details related to analytical techniques for frequency discrimination that may be employed for evaluating weld quality are known to one of ordinary skill in the art, and thus not described in further detail.

Figure 4:
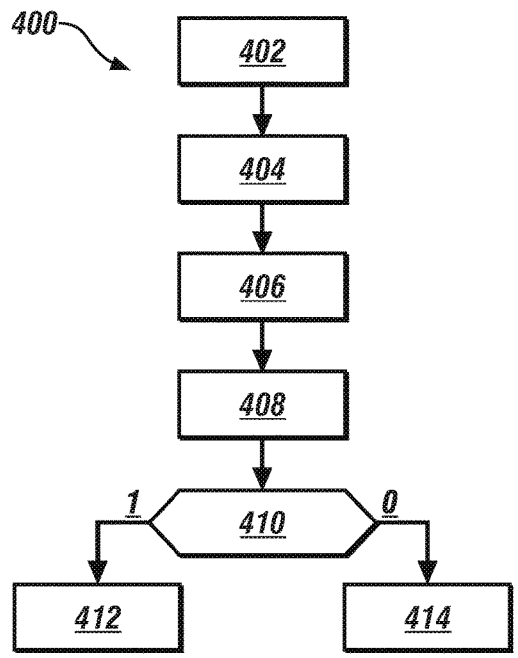
FIG. 4 schematically shows a first stress test routine that may be executed in a controller to employ the first embodiment of the test fixture described with reference to FIG. 2 to non-destructively evaluate a workpiece in the form of the battery cell described with reference to FIGS. 1A and 1B, in accordance with the disclosure.

FIG. 4 schematically shows a stress test routine 400 that may be executed by or through the test fixture controller 280 to non-destructively evaluate a workpiece in the form of the battery cell 10 described with reference to FIGS. 1A and 1B, employing the test fixture 200 described with reference to FIG. 2. More specifically, the stress test routine 400 may be advantageously applied to evaluate the one of the weld junctions between one of the terminals 20, 22 and the plurality of electrode foils 16 on the battery cell 10, e.g., the weld junction 18 that is associated with terminal 20. Table 1 is provided as a key wherein the numerically labeled blocks and the corresponding functions are set forth as follows, corresponding to the stress test routine 400. Those having ordinary skill in the art will recognize that the teachings may be described herein in terms of functional and/or logical block components and/or various processing steps. It should be realized that such block components may be composed of any number of hardware, software, and/or firmware components configured to perform the specified functions.

TABLE 1

| BLOCK | BLOCK CONTENTS |
| --- | --- |
| 402 | Insert workpiece into the first clamping device of the test fixture, retain the workpiece with the first clamping device, clamp one of the terminals of the workpiece with the terminal gripper, and attach electrical probes to both terminals |
| 404 | Apply pre-tension to the clamped terminal |
| 406 | Operate the dynamic stress end effector |
| 408 | Monitor impedance and weld temperature |
| 410 | Evaluate integrity of the weld junction of the workpiece |
| 412 | Indicate weld junction is acceptable |
| 414 | Indicate weld junction is unacceptable |

Execution of the stress test routine 400 may proceed as follows. The steps of the stress test routine 400 may be executed in any suitable order, and are not limited to the order described with reference to FIG. 4. As indicated, the stress test routine 400 includes inserting a workpiece in the form of an embodiment of the battery cell 10 into the first clamping device 220 of the test fixture 200. The cell body 14 of the battery cell 10 is clamped or otherwise retained by the first clamping device 220, one of the positive and negative terminals 20, 22 of the battery cell 10 is clamped by the terminal gripper 230 of the dynamic stress end effector 240, and electrical probes 292, 294 are electrically connected to respective terminals 20, 22 (402). A pre-tension load is applied to one of the positive and negative terminals 20, 22 by the dynamic stress end effector 240 to remove any slack between the one of the terminals 20, 22 and the cell body 14 (404). Once the clamping is complete and any residual slack is removed, the dynamic stress end effector 240 is operated to apply a repetitive stress by applying ultrasonic vibration at the one of the positive and negative terminals 20, 22 of the battery cell 10. The purpose of applying ultrasonic vibration at the one of the positive and negative terminals 20, 22 of the battery cell 10 is to apply stress to the weld junction of the battery cell 10. The applied stress serves to weaken a poorly executed weld junction, and thus increase the likelihood that an unacceptable weld junction is identified before further processing of the battery cell 10. The ultrasonic vibration is preferably applied in a direction that is parallel to the longitudinal axis 24 of the battery cell 10, and is a repetitively-executed linear oscillatory motion that is applied at a frequency that is within a range between 10 kHz and 100 kHz, at an amplitude that is preferably within a range between several micrometers and one hundred micrometers, for a duration of time between 0.5 s and 10 s (406).

Simultaneous with the application of the ultrasonic vibration, the cell monitoring controller 290 monitors impedance of the battery cell 10 across the positive and negative terminals 20, 22 (408). Monitoring impedance of the battery cell 10 includes applying a current of known magnitude across the positive and negative terminals 20, 22 and monitoring voltage. A magnitude for impedance may be determined based upon the relationship between current, voltage, and impedance, i.e., $V=I*R$. In one embodiment, a single-frequency sine wave current may be applied across the terminals 20, 22 of the battery cell 10, e.g., around 500 Hz, which yields a sine wave voltage having the same frequency but shifted in phase and amplitude. The test fixture controller 280 includes control routines to evaluate the sine wave current and the sine wave voltage signals to determine the impedance. In addition, simultaneous with the application of the ultrasonic vibration, the cell monitoring controller 290 may monitor a temperature profile at or near the weld junction of the clamped one of the terminals 20, 22 of the battery cell 10, which is output from the thermal probe 296.

The impedance across the terminals 20, 22, and, in certain embodiments, the temperature at or near the respective weld junction in embodiments employing the thermal probe 296 are employed to evaluate integrity of the weld junction, e.g., weld junction 18, based upon the applied ultrasonic vibration (410).

When the measured impedance is less than a threshold impedance, it indicates that the integrity of the weld junction associated with the clamped one of the terminals 20, 22 of the battery cell 10, e.g., weld junction 18, has been maintained (410)(1), the tested one of the terminals 20, 22 of the battery cell 10 is identified as acceptable (412). This determination of an acceptable weld junction may be determined in conjunction with an evaluation that the monitored temperature profile is less than a threshold temperature.

The process described with reference to steps 402 through 412 is repeated for the other one of the terminals 20, 22.

When the measured impedance is greater than or equal to the threshold impedance, it indicates that the integrity of the weld junction associated with the clamped one of the terminals 20, 22 of the battery cell 10, e.g., weld junction 18, has been compromised (410)(0). The battery cell 10 is identified as an unacceptable part and rejected (414). When the weld junctions associated with both of the terminals 20, 22 are identified as being acceptable, the workpiece may be identified as acceptable and removed from the test fixture 200 for assembly into a battery pack or other device. When one of the weld junctions associated with one of the terminals 20, 22 has been identified as being unacceptable, the workpiece may be identified as unacceptable, removed from the test fixture 200 and removed from further assembly operations pending further evaluation. Compromised integrity of a weld junction may include a weld fracture, a tearing of material in the area of the weld junction, or another fault. Such weld junction faults are known to one of ordinary skill in the art.

Figure 5:
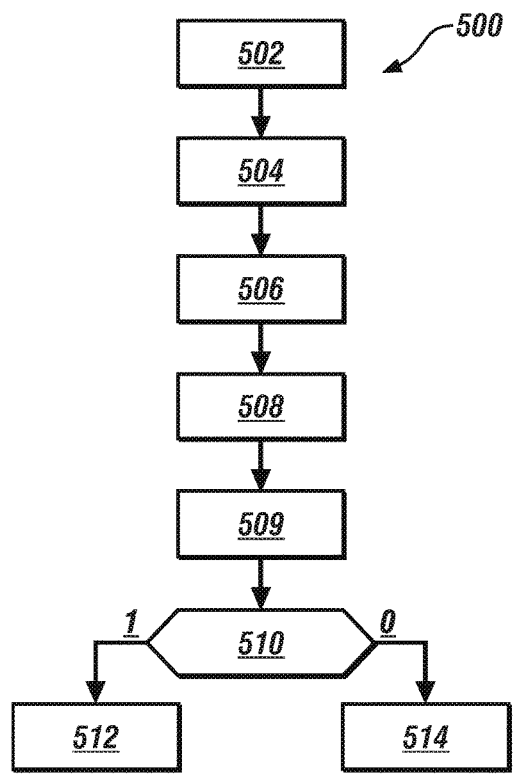
FIG. 5 schematically shows a second stress test routine that may be executed in a controller to employ the second embodiment of the test fixture described with reference to FIG. 3 to non-destructively evaluate a workpiece in the form of the battery cell described with reference to FIGS. 1A and 1B, in accordance with the disclosure.

FIG. 5 schematically shows a stress test routine 500 that may be executed by or through the test fixture controller 280 to non-destructively evaluate a workpiece in the form of the battery cell 10 described with reference to FIGS. 1A and 1B, employing the test fixture 300 described with reference to FIG. 3. More specifically, the stress test routine 500 may be advantageously applied to evaluate the one of the weld junctions between one of the terminals 20, 22 and the plurality of electrode foils 16 on the battery cell 10, e.g., weld junction 18 that is associated with terminal 20. Table 2 is provided as a key wherein the numerically labeled blocks and the corresponding functions are set forth as follows, corresponding to the stress test routine 500. Those having ordinary skill in the art will recognize that the teachings may be described herein in terms of functional and/or logical block components and/or various processing steps. It should be realized that such block components may be composed of any number of hardware, software, and/or firmware components configured to perform the specified functions.

TABLE 2

| BLOCK | BLOCK CONTENTS |
| --- | --- |
| 502 | Insert workpiece into the first clamping device of the test fixture, retain the workpiece with the first clamping device, clamp one of the terminals of the workpiece with the terminal gripper, and attach electrical probes to both terminals |
| 504 | Apply pre-tension to the clamped terminal |
| 506 | Operate the dynamic stress end effector |
| 508 | Monitor impedance |
| 509 | Apply tension force to weld junction and monitor impedance |
| 510 | Evaluate integrity of the weld junction of the workpiece |
| 512 | Indicate weld junction is acceptable |
| 514 | Indicate weld junction is unacceptable |

Execution of the stress test routine 500 may proceed as follows. The steps of the stress test routine 500 may be executed in any suitable order, and are not limited to the order described with reference to FIG. 5. As indicated, the stress test routine 500 includes inserting a workpiece in the form of an embodiment of the battery cell 10 into the first clamping device 220 of the test fixture 300. The cell body 14 of the battery cell 10 is clamped or otherwise retained by the first clamping device 220, one of the positive and negative terminals 20, 22 of the battery cell 10 is clamped by the terminal gripper 230 of the dynamic stress end effector 240, and electrical probes 292, 294 are electrically connected to respective terminals 20, 22 (502). A pre-tension load is applied to the one of the terminals 20, 22 by the dynamic stress end effector 240 to remove any slack between the one of the terminals 20, 22 and the cell body 14 (504). Once the clamping is complete and any residual slack is removed, the dynamic stress end effector 240 is operated to apply a repetitive stress by applying ultrasonic vibration at the one of the positive and negative terminals 20, 22 of the battery cell 10. The ultrasonic vibration is preferably applied in a direction that is parallel to the longitudinal axis 24 $f$ the battery cell 10, and is a repetitively-executed linear oscillatory motion that is applied at a frequency that is within a range between 10 kHz and 100 kHz, at an amplitude that is preferably within a range between several micrometers and one hundred micrometers, for a duration of time between 0.5 s and 10 s (506).

Simultaneous with the application of the ultrasonic vibration, the cell monitoring controller 295 monitors impedance of the battery cell 10 across the positive and negative terminals 20, 22 (508). As previously described, monitoring impedance of the battery cell 10 includes applying a current of known magnitude across the positive and negative terminals 20, 22 and monitoring voltage. A magnitude for impedance may be determined based upon the relationship between current, voltage, and impedance, i.e., $V=I*R$. In one embodiment, a single-frequency sine wave current may be applied across the terminals 20, 22 of the battery cell 10, e.g., around 500 Hz, which yields a sine wave voltage having the same frequency but shifted in phase and amplitude. The test fixture controller 280 includes control routines to evaluate the sine wave current and the sine wave voltage signals to determine the impedance.

Subsequent to the application of the ultrasonic vibration, the cell monitoring controller 295 commands the cell tensioning device 270 to exert a tensile force on the elements of the battery cell 10 at or near the weld junction 18 employing the first member 272, second member 274 and actuators 276, coincident with monitoring the impedance of the battery cell 10 across the positive and negative terminals 20, 22 (509). The impedance across the positive and negative terminals 20, 22 is employed to evaluate integrity of the weld junction, e.g., weld junction 18, based upon the applied ultrasonic vibration (510).

When the measured impedance is less than a threshold impedance, it indicates that the integrity of the weld junction associated with the clamped one of the terminals 20, 22 of the battery cell 10, e.g., weld junction 18, has been maintained (510)(1), the tested one of the terminals 20, 22 of the battery cell 10 may be identified as acceptable (512).

The process described with reference to steps 502 through 512 is repeated for the other one of the terminals 20, 22. When the measured impedance is greater than or equal to the threshold impedance, it indicates that the integrity of the weld junction associated with the clamped one of the terminals 20, 22 of the battery cell 10, e.g., weld junction 18, may have been compromised (510)(0). The battery cell 10 is identified as an unacceptable part and rejected (514). When welds associated with both of the terminals 20, 22 are identified as being acceptable, the workpiece is identified as acceptable and is removed from the test fixture 200 for assembly into a battery pack or other device. When one of the welds associated with one of the terminals 20, 22 has been identified as being unacceptable, the workpiece is identified as unacceptable and is removed from the test fixture 200 and removed from further assembly pending further evaluation.

The flowchart and block diagrams in the flow diagrams illustrate the architecture, functionality, and operation of possible implementations of systems, methods, and computer program products according to various embodiments of the present disclosure. In this regard, each block in the flowchart or block diagrams may represent a module, segment, or portion of code, which comprises one or more executable instructions for implementing the specified logical function(s). It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The detailed description and the drawings or figures are supportive and descriptive of the present teachings, but the scope of the present teachings is defined solely by the claims. While some of the best modes and other embodiments for carrying out the present teachings have been described in detail, various alternative designs and embodiments exist for practicing the present teachings defined in the appended claims.

The invention claimed is:

1. A method for evaluating a battery cell composed of a cell body having a plurality of electrode foils joined to a positive terminal and a negative terminal, wherein the positive terminal and the negative terminal are each joined to the electrode foils at weld junctions, the method comprising:
   retaining the cell body of the battery cell in a first clamping device;
   gripping one of the positive and negative terminals in a terminal gripper;
   applying, employing a dynamic stress end effector coupled to the terminal gripper, a vibrational excitation load to the one of the positive and negative terminals;
   monitoring, via a controller, impedance between the positive terminal and the negative terminal; and
   evaluating integrity of the weld junction of the one of the positive and negative terminals based upon the impedance.

2. The method of claim 1, wherein the impedance between the positive terminal and the negative terminal is monitored subsequent to applying the vibrational excitation load to the one of the positive and negative terminals.

3. The method of claim 1, wherein the impedance between the positive terminal and the negative terminal is monitored coincident with the applying the vibrational excitation load to the one of the positive and negative terminals.

4. The method of claim 1, further comprising:
   thermally monitoring the weld junction of the one of the positive and negative terminals coincident with applying the vibrational excitation load to the one of the positive and negative terminals; and
   evaluating integrity of the weld junction based upon the cell impedance and the thermal monitoring of the weld junction.

5. The method of claim 1, wherein evaluating integrity of the weld junction based upon the monitored cell impedance further comprises:
   inducing a tensile force at the weld junction in a direction that is orthogonal to a longitudinal axis of the weld junction and coincidentally monitoring the cell impedance; and
   evaluating integrity of the weld junction based upon the monitored cell impedance.

6. The method of claim 1, wherein the plurality of electrode foils and the weld junction are contained within a sealed pouch of a cell body and the positive and negative terminals protrude from the cell body.

7. The method of claim 1, wherein applying the vibrational excitation load to the terminal comprises applying an ultrasonic vibrational load to the terminal.

8. The method of claim 7, wherein the ultrasonic vibrational load is applied to the terminal in a direction that is parallel to the longitudinal axis of the battery cell.

9. The method of claim 7, wherein the ultrasonic vibrational load comprises an oscillatory motion that is applied at a frequency that is within a range between 10 kHz and 100 kHz.

10. The method of claim 7, wherein the ultrasonic vibrational load comprises a repetitively-executed linear oscillatory motion that is applied at an amplitude that is preferably within a range between several micrometers and one hundred micrometers.

11. The method of claim 7, wherein the ultrasonic vibrational load comprises an oscillatory motion that is applied for a duration of time between 0.5 s and 10 s.

12. The method of claim 1, wherein applying a static load to the terminal comprises applying a preset static tensile load between the terminal and the cell body, wherein the static load is propagated through the terminal to the electrode foils through the weld junction.

13. The method of claim 1, wherein monitoring, via a controller, impedance between the positive terminal and the negative terminal comprises
   applying a current having a known magnitude across the positive terminal and the negative terminal; and
   monitoring the voltage between the positive terminal and the negative terminal.

14. The method of claim 13, further comprising:
   applying a current having s single-frequency sine wave current having a known magnitude across the positive terminal and the negative terminal; and
   monitoring an amplitude and a phase shift of the voltage between the positive terminal and the negative terminal.

15. A method for evaluating a weld junction joining one of a positive and a negative terminal to a plurality of electrode foils of a battery cell, the method comprising:
   retaining the battery cell in a first clamping device;
   gripping one of the positive and negative terminals in a terminal gripper;
   applying an ultrasonic vibrational load to the terminal gripper employing a dynamic stress end effector coupled to the terminal gripper;
   monitoring, via a controller, impedance between the positive terminal and the negative terminal; and
   evaluating integrity of the weld junction of the one of the positive and negative terminals based upon the impedance.

* * * * *